(12) United States Patent
Niehaus et al.

(10) Patent No.: US 7,927,827 B2
(45) Date of Patent: Apr. 19, 2011

(54) DETECTION AND AMPLIFICATION OF LIGANDS

(75) Inventors: Gary D. Niehaus, Kent, OH (US); Christopher J. Woolverton, Kent, OH (US); Kathleen J. Doane, Ravenna, OH (US); Steven P. Schmidt, Akron, OH (US); Steven A. Signs, Hudson, OH (US)

(73) Assignee: Kent State University, Kent, OH (US)

( * ) Notice: Subject to any disclaimer, the term of this patent is extended or adjusted under 35 U.S.C. 154(b) by 587 days.

(21) Appl. No.: 11/751,065

(22) Filed: May 21, 2007

(65) Prior Publication Data

US 2007/0218508 A1 Sep. 20, 2007

Related U.S. Application Data

(60) Division of application No. 10/133,610, filed on Apr. 26, 2002, now Pat. No. 7,267,957, which is a continuation of application No. 09/633,327, filed on Aug. 7, 2000, now abandoned, which is a continuation of application No. 09/095,196, filed on Jun. 10, 1998, now Pat. No. 6,171,802.

(51) Int. Cl.
*G01N 33/53* (2006.01)
*C12Q 1/00* (2006.01)

(52) U.S. Cl. ........... 435/7.9; 435/7.8; 435/174; 435/182

(58) Field of Classification Search .................. 435/7.9, 435/7.8, 174, 182
See application file for complete search history.

(56) References Cited

U.S. PATENT DOCUMENTS

| | | | |
|---|---|---|---|
| 3,817,837 A | 6/1974 | Rubenstein et al. | |
| 3,975,237 A | 8/1976 | Rubenstein et al. | |
| 4,067,774 A | 1/1978 | Rubenstein et al. | |
| 4,203,802 A | 5/1980 | Rubenstein et al. | |
| 4,600,690 A | 7/1986 | Karmen et al. | |
| 4,604,364 A | 8/1986 | Kosak | |
| 4,693,970 A | 9/1987 | O'Connell et al. | |
| 4,904,592 A * | 2/1990 | Freeman et al. | 435/183 |

(Continued)

FOREIGN PATENT DOCUMENTS

DE 3617710 12/1988

(Continued)

OTHER PUBLICATIONS

Mirza et al. Entrapment of Nonproteolytic enzymes in alpha-2 macroglobulin using immobilized trypsin. Analytical Biochemistry 213, 133-139 (1993).*

(Continued)

*Primary Examiner* — Jacob Cheu
*Assistant Examiner* — Pensee T Do
(74) *Attorney, Agent, or Firm* — Scott M. Oldham, Esq.; Hahn Loeser + Parks LLP

(57) ABSTRACT

A system for the detection of ligands comprising at least one receptor and an amplification mechanism coupled to the receptor wherein an amplified signal is produced as a result of receptor binding a ligand. Examples of suitable amplification mechanisms include antibody-embedded liquid crystalline materials; use of alpha-2-macroglobulin to encage an enzyme, whereby the enzyme is separated from its substrate by an receptor; and a receptor engineered to inhibit the active site of an enzyme only in the absence of a ligand. Also provided are methods for the automatic detection of ligands.

10 Claims, 9 Drawing Sheets

U.S. PATENT DOCUMENTS

| | | | |
|---|---|---|---|
| 4,943,525 | A | 7/1990 | Dawson |
| 5,149,626 | A | 9/1992 | Fleming |
| 5,252,459 | A | 10/1993 | Tarcha et al. |
| 5,447,837 | A | 9/1995 | Urnovitz |
| 5,596,434 | A | 1/1997 | Walba |
| 5,681,571 | A | 10/1997 | Holmgren et al. |
| 6,001,571 | A | 12/1999 | Mandecki |
| 6,171,802 | B1 | 1/2001 | Woolverton et al. |
| 6,284,197 | B1 | 9/2001 | Abbott et al. |
| 6,342,588 | B1 | 1/2002 | Osbourn et al. |
| 6,362,328 | B1 | 3/2002 | Fisher et al. |
| 6,482,517 | B1 | 11/2002 | Anderson |
| 6,524,665 | B2 | 2/2003 | Sahouani et al. |
| 2002/0052002 | A1 | 5/2002 | Niehaus et al. |

FOREIGN PATENT DOCUMENTS

| | | |
|---|---|---|
| WO | WO95/33803 | 12/1995 |

OTHER PUBLICATIONS

Bernfeld et al. Antigens and Enzymes made insobuble by entrapping them into lattices of synthetic polymers. Science, vol. 142, 678-679, Nov. 8, 1963.*

Born, Max and Wolf, E. Principles of Optics, Sixth Edition, Pergamon Press, Oxford, pp. 665-703 (1980).

Demus, D. Goodby, J. Gray, G.W., Spiess, H.-W., and Vill, V. Handbook of Liquid Crystals, vol. 2 B, Wiley-VCH Verlag GmbH:Weinheim, Federal Republic of Germany (1998).

Deng, Su-Jun, et al. "Basis for Selection of Improved Carbohydrate-Binding Single-Chain Antibodies from Synthetic Gene Libraries." Proc. Natl. Acad. Sci. USA, vol. 92, pp. 4992-4996 (May 1995).

Griffiths, Andrew D., et al. "Human Anti-Self Antibodies with High Specificity from Phage Display Libraries," The EMBO Journal, vol. 12, No. 2, pp. 725-734 (1993).

Gupta, V.K., et al., "Design of Surfaces for Patterned Alignment of Liquid Crystals on Planar and Curved Substrates." Science, vol. 276, pp. 1533-1536 (1997).

Gupta, V.K., et al. "Optical Amplification of Ligand-Receptor Binding Using Liquid Crystals." Science, vol. 279, pp. 2077-2080 (Mar. 27, 1998).

Harlow and Lane. Antibodies. A Laboratory Manual. Cold Spring Harbor Laboratory, Chapter 6, pp. 141-142 (1988).

Holliger, Phillpp. "Diabodies: Small Bivalent and Bidpecific Antibody Fragments." Proc. Natl. Acad. Sci. USA, vol. 90, pp. 6444-6448 (Jul. 1993).

Hou, Zhizhong, Abbott, Nicholas L., and Stroeve, Pieter. "Electroless Gold as a Substrate for Self-Assembled Monolayers." Langmuir, vol. 14, pp. 3267-3297 (1998).

Lydon, John. "Chromonic liquid crystal phases." Curr. Opin. Colloid Interface Sci., vol. 3, No. 5, pp. 458-466 (1988).

Marks, James D., et al. "By-Passing Immunization Human Antibodies from V-gene Libraries Displayed on Phage." J. Mol. Biol., vol. 222, pp. 581-597 (1991).

Nastishin, Yu A. "Brine-Rich Corner of the Phase Diagram of the Ternary System Cetylpyridinium Chloride-Hexanol-Brine." Langmuir, vol. 12, pp. 5011-5015 (1996).

Proc. Natl. Acad. Sci. USA, vol. 92, pp. 6439-6443 (Jul. 1995).

Seabrook, R. and Atkinson, Modified Antibodies. Stockton Press, pp. 53-77 (1991).

Sevier et al. "Monoclonal Antibodies in Clinical Immunology." Clinical Chemistry, vol. 27, No. 11, pp. 1797-1805 (1981).

Sutherland, R., et al. "Surface effect immunoassay." Stockton Press, pp. 515-542 (1991).

Winter, Greg, et al. "Making Antibodies by Phage Display Technology." Annul. Rev. Immunol., vol. 12, pp. 433-455 (1994).

* cited by examiner

DETECTION AND AMPLIFICATION OF LIGANDS

This application is a divisional of U.S. patent application Ser. No. 10/133,610, filed Apr. 26, 2002, which is a continuation of abandoned patent application Ser. No. 09/633,327, filed Aug. 7, 2000, which is a continuation of prior application Ser. No. 09/095,196, filed Jun. 10, 1998, now U.S. Pat. No. 6,171,802. application Ser. Nos. 10/133,610, 09/633,327 and 09/095,196 are hereby incorporated by reference.

TECHNICAL FIELD OF THE INVENTION

The present invention generally relates to the detection of a ligand by a receptor. More specifically, the present invention relates to highly specific receptors and the incorporation of these receptors into an amplification mechanism for the rapid and automatic detection of the ligand, particularly pathogens and/or their toxins.

BACKGROUND OF THE INVENTION

The detection of a ligand by a receptor (for example, detection of a pathogenic agent such as a microbe or toxin by an antibody; or detection of an antibody in blood by another antibody; or binding of a chemical toxin, such as nerve gas, to its receptor) is important in the diagnosis and treatment of individuals exposed to disease-causing agents. Early detection of pathogenic agents can be a great benefit in either disease prophylaxis or therapy before symptoms appear or worsen.

Every species, strain or toxin of a microbe contains unique surface ligands. Using molecular engineering and/or immunological techniques, receptor molecules, such as antibodies, can be isolated that will bind to these ligands with high specificity. Methods have also been developed where receptors, such as antibodies, are linked to a signaling mechanism that is activated upon binding. Heretofore, however, no system has been developed that can quickly and automatically detect and amplify a receptor signal coming from the binding of a single or a low number of ligands. Such a system is imperative for rapid and accurate early detection of ligands.

Most available diagnostic tests are antibody based, and can be used to detect either a disease-causing agent or a biologic product produced by the patient in response to the agent. There are currently three prevailing methods of antibody production for recognition of ligands (antigens): polyclonal antibody production in whole animals with recognition for multiple epitopes, monoclonal antibody production in transformed cell lines with recognition for a single epitope (after screening), and molecularly engineered phage displayed antibody production in bacteria with recognition of a single epitope (after screening). Each of these receptor systems is capable of binding and identifying a ligand, but the sensitivity of each is limited by the particular immunoassay detection system to which it is interfaced.

Immunoassays, such as enzyme-linked immunosorbent assay (ELISA), enzyme immunoassay (EIA), and radioimmunoassay (RIA), are well known for the detection of antigens. The basic principle in many of these assays is that an enzyme-, chromogen-, fluorogen-, or radionucleotide-conjugated antibody permits antigen detection upon antibody binding. In order for this interaction to be detected as a color, fluorescence or radioactivity change, significant numbers of antibodies must be bound to a correspondingly large number of antigen epitopes.

Thus, there is a need for a system that rapidly, reliably, and automatically detects ligands, especially when present in very small quantities and consequently provides a measurable signal.

SUMMARY OF THE INVENTION

It is therefore an object of the present invention to provide a system that will detect a ligand with high sensitivity and high specificity.

It is another object of the present invention to provide a system that will amplify a signal produced by the binding of a ligand to a receptor.

It is another object of the present invention to provide a caged enzyme amplification mechanism.

It is yet a further object of the present invention to provide a system that will activate an enzyme inactivated by a bound receptor.

It is still a further object of the present invention to provide a system that will distort a liquid crystal array upon the binding of a ligand to a receptor.

It is still yet a further object of the present invention to provide a detection device that will continuously monitor the environment or the body and signal its possessor when a ligand is present.

In general, the present invention provides a system for the detection and amplification of ligands, such as pathogenic agents, comprising at least one receptor and an amplification mechanism coupled to that receptor, wherein an amplified signal is produced as a result of the receptor binding the ligand.

DETAILED DESCRIPTION OF THE PREFERRED EMBODIMENT

Figure 1A:
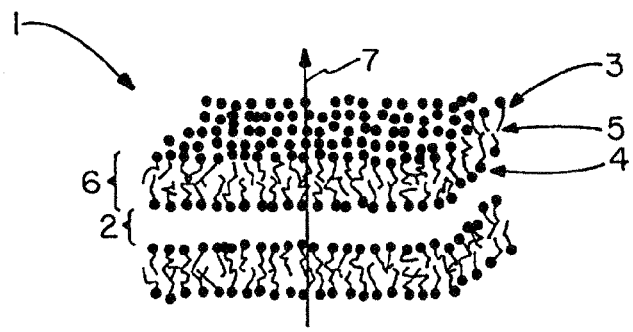
FIG. 1A is a schematic representation of the lamellar structure of a lyotropic liquid crystal formed by alternating layers of water and biphilic molecules.

In the present invention, ligand-specific receptors are interfaced with an amplification mechanism such that a receptor-ligand interaction changes the conformation of the receptor and produces a signal. Amplification preferably occurs through a calorimetric, fluorometric or birefringent shift that can be photometrically detected. The detected signal may then be electronically amplified to automate the system.

Ligand Detection Component

Any receptor, such as antibodies or biologic/biologically engineered receptors for ligands, can be incorporated into the device as long as binding of the ligand to the receptor causes a detectable distortion of the receptor. For example, any type of monospecific antibody (polyclonal, monoclonal, or phage displayed) can effectively function as a receptor, and thus each of those antibody types will be described in the following paragraphs. Although phage-displayed antibodies can be expeditiously modified for identification of new ligands and are used as receptor examples in this patent application, any physically-distortable receptor-ligand interaction is appropriate for the detection component.

Polyclonal antibodies: Antibody-based antigen detection has been exploited for several decades. Injection of a purified ligand (antigen) into a host animal stimulates the immune system to produce an array of antibodies against various reactive sites on the antigen. Since several lymphocytes are responding to different antigenic epitopes, a multi-specific antibody cocktail (polyclonal) is created and can be purified for antigen detection.

Monoclonal antibodies: Antibody-producing spleen cells (B lymphocytes) are fused with immortalized myeloma cells to create hybridomas which provide nearly infinite quantities of antibody with a single, defined specificity. Interstrain and even interspecies hybrids of these 'monoclonal' antibodies can be generated through genetic engineering techniques. These highly specific antibodies have significant therapeutic potential, as evidenced by the U.S. Food and Drug Administration's approval of the use of mouse-human chimeric antibodies for treatment of selected diseases.

Phage-displayed mono-specific antibodies: Phage-displayed techniques will be used to isolate single chain chimeric antibodies to various pathogenic agents. The genomic DNA of the B lymphocyte contains the code to produce an antibody to virtually all possible ligands (antigens). In a phage displayed antibody system (PDA), DNA encoding a single chain chimera of the native antibody's hypervariable ligand-binding region is synthesized by joining DNA encoding an antibody heavy chain and DNA encoding an antibody light chain and inserting therebetween DNA encoding a linker region. The desired amino acid sequence of the linker region depends on the characteristics required for any given amplification mechanism. The linker region may have to be able to interact and/or bond to a protein or other substance. Therefore, the polypeptide sequence may have to have, for example, a particular conformation, specifically placed functional groups to induce ionic or hydrogen bonds, or a hydrophobicity that is compatible with the amplification mechanism. Regardless of the type of amplification mechanism, however, the linker region plays a critical role in interfacing the amplification mechanism to the receptor.

The DNA, preferably human or mouse, encoding the single chain chimeric antibody is cloned into a bacteriophage (phage) vector using well-known techniques (Marks et al., J. Mol. Bio. Vol. 222:581 (1991); Griffiths et al., EMBO J. 12:725 (1993); and Winters et al., Ann. Rev. Immunol. 12:433 (1994)), incorporated herein by reference. The single chain chimeric antibodies then become displayed on the surface of a filamentous phage with the hypervariable antigen-binding site extended outward.

After the addition of ligands, phage that are reactive against non-targeted ligands are subtracted from the phage library using known techniques (Marks et al., J. Mol. Bio. Vol. 222: 581 (1991); Griffiths et al., EMBO J. 12:725 (1993); and Winters et al., Ann. Rev. Immunol. 12:433 (1994)), incorporated herein by reference. The remaining phage are reacted with their specific ligand and phage reactive with that specific ligand eluted. Each of these phage are then isolated and expressed in a bacterial host, such as *Escherichia coli* (*E. coli*) to produce a large quantity of phage containing the desired surface-displayed antibody. Each of the aforementioned methods relating to synthesizing and cloning DNA, subtracting phages, isolating and expressing phages and recovering viral DNA are well known and fully described by Marks et al., J. Mol. Biol. (1991); Griffiths et al., EMBO J. 12:725 (1993); and Winters et al., Ann. Rev. Immunol. 12:433 (1994), all of which are incorporated herein by reference.

Amplification Component

Any mechanism that permits detection of ligand-receptor complex formation functions as an amplifier and can be incorporated into the device. Three amplification mechanisms are proposed. First, a liquid crystal will amplify the distortion caused when a ligand binds to a receptor. Second, an enzyme will be placed in a biologic cage and a receptor will be attached to the biologic cage to prevent enzyme-substrate interaction. Ligand attachment to the receptor will open a substrate channel, resulting in enzyme-substrate interaction, and thus permitting detectable levels of reaction product. Third, the linker region of a receptor, such as a phage-displayed antibody, will be engineered to bind and inhibit the active site of an enzyme. Dissociation of the receptor-enzyme complex occurs upon formation of an receptor-ligand complex, such as an antigen-antibody complex, and results in activation of the enzyme and generation of product.

Liquid Crystal: A liquid crystal is a state of matter in which molecules exhibit some orientational order but little positional order. This intermediate ordering places liquid crystals between solids (which possess both positional and orientational order) and isotropic fluids (which exhibit no long-range order). Solid crystal or isotropic fluid can be caused to transition into a liquid crystal by changing temperature (creating a thermotropic liquid crystal) or by using an appropriate diluting solvent to change the concentration of solid crystal (creating a lyotropic liquid crystal). Lyotropic liquid crystals will be used for our amplification system.

As seen in FIG. 1A, most lyotropic liquid crystals, designated generally by the numeral 1, are formed using water 2 as a solvent for biphilic molecules 3, for example, molecules which possess polar (hydrophilic) aliphatic parts 4 and apolar (hydrophobic) aliphatic parts 5. When water 2 is added to a biphilic molecule 3, such as the cationic surfactant cetylpiridinium chloride [$C_{21}H_{38}ClN$], a bilayer 6 forms as the hydrophobic regions coalesce to minimize interaction with water 2 while enhancing the polar component's interaction with water. The concentration and geometry of the specific molecule define the supramolecular crystalline order of the liquid crystal. The molecules can aggregate into lamellae as well as disk-like or rod-like micelles that form a nematic or cholesteric phase. The $C_{21}H_{38}ClN$ forms a lamella of alternating layers of water and biphilic molecules. An orientational order is created by the alternating layers of water and biphilic molecules and thus the liquid crystal is opaque (exhibits optical anisotropy) to polarized light 7 provided by a light source located perpendicular to the plane of the liquid crystal.

Figure 1B:
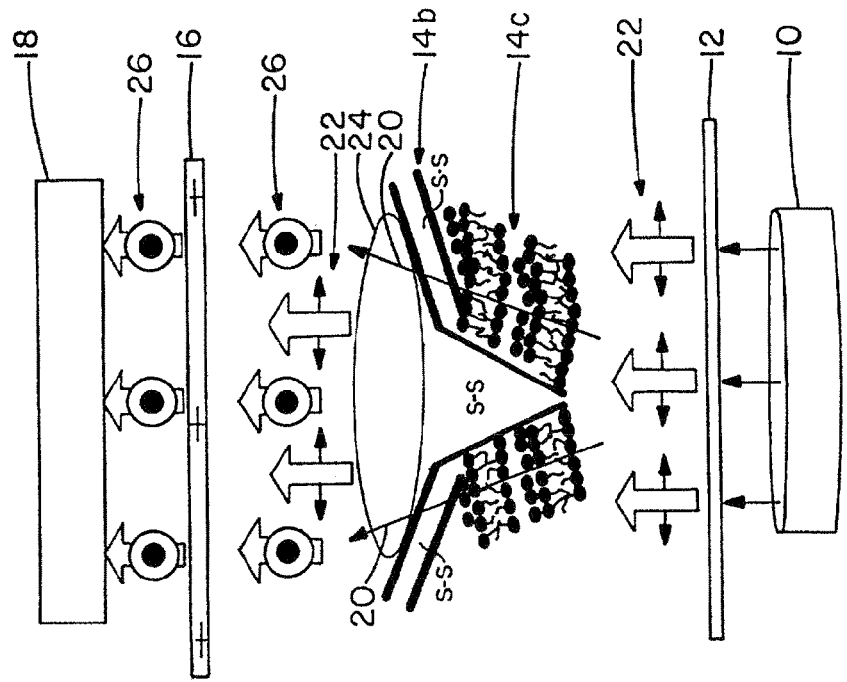
FIG. 1B is a schematic representation of the amplification mechanism with a receptor inserted into the lyotropic liquid crystal.
Figure 1C:
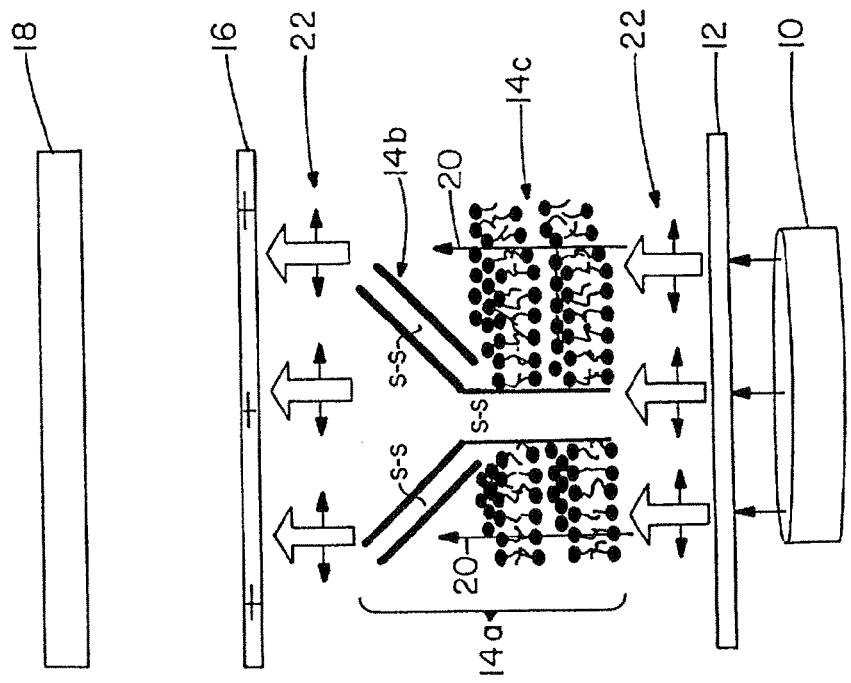
FIG. 1C is a schematic representation of the amplification mechanism with the specific ligand bound to its receptor causing deformation of the liquid crystal and alteration of the transmission of polarized light.

Most biologic receptors possess both hydrophilic and hydrophobic regions and thus readily incorporate into biphilic lyotropic liquid crystals. Additionally, the inactivated receptors do not destroy the optical anisotropy of the liquid crystal and therefore, the receptor-enriched liquid crystal remains opaque to polarized light (FIG. 1B). However, optical anisotropy is disrupted when receptor conformation shifts as during the formation of the receptor-ligand complex (FIG. 1C). The elasticity of the liquid crystal enhances the local distortions in the vicinity of the receptor-ligand complex, and expands it to an optically detectable, supramicron scale. Biologic materials can be detected on the surface of thermotropic liquid crystals (V. K. Gupta et al., Science 279:277-2080, 1998). However, lyotropic liquid crystals readily incorporate ligand-specific receptors, and are thus clearly superior for detection of biologic molecules.

Configurations of Ligand Detection System

By way of example, one envisioned application of the present invention is in a multiwell system. Each well of the system would contain PDAs to a specific ligand, such as a pathogenic microbe, interfaced with an amplification mechanism of the present invention. When the microbial agent interacts with the antibody, the resulting antibody distortion triggers the amplification mechanism. Preferably, the amplified signal is then transduced into a perceptible signal. Accordingly, it is envisioned that such a system could be placed in a physician's office, and be used in routine diagnostic procedures. Alternatively, such a system could be placed on or near soldiers in battle, and the invention used to alert the soldiers to the presence of a toxic agent. It is further envisioned that a multiwell system, although it can be used with other embodiments, such as the luciferase or the caged enzyme described hereinbelow, is preferably used in conjunction with the liquid crystal embodiment described herein.

Thus, in one embodiment of the present invention, shown schematically in FIGS. 1B and 1C, a lyotropic liquid crystalline material is used as an amplification mechanism. As shown in FIG. 1B, the device consists of a light source 10, an initial polarizer 12, with the direction of polarization in the plane of the figure, a pathogen detection system 14a, comprising Nonspecific antibodies 14b embedded in biphilic, lyotropic liquid crystalline material 14c, a secondary polarizer 16, with the direction of polarization perpendicular to the plane of the figure, and a photodetector 18.

In operation, the initial polarizer 12 organizes a light stream 22 that is linearly polarized in the plane of the figure. The optical axis 20 of the inactivated device is perpendicular to the pathogen detection system 14a, and thus no birefringence of the transluminating linearly polarized light stream 22 occurs. Since the polarization direction of the secondary polarizer 16 is perpendicular to the transluminating linearly polarized light 22, the secondary polarizer prevents light from reaching the photodetector 18.

Binding of a ligand 24, such as a microbe, to the receptor 14b, such as an antibody, distorts the liquid crystal 14c, induces birefringence and thus causes the generation of detectable light. This activation process is illustrated in FIG. 1C. The receptor (antibody) 14b is embedded in the biphilic, lyotropic liquid crystal 14c. The spacial distortion caused by the formation of the antigen-antibody complex is transmitted to the contiguous liquid crystal 14c. The elastic characteristics of the liquid crystal permit the distortion to be transmitted over a region much larger than the size of the receptor-ligand complex. This allows the use of the standard optical phenomenon of birefringence to detect distortions caused by the receptor-ligand complex. The altered liquid crystalline order tilts the optical axis 20 and induces birefringence. In other words, the incident polarized light 22 gives rise to two refracted light waves: the ordinary wave and the extraordinary wave with the mutually orthogonal polarizations (see, Max Born and E. Wolf., Principals of Optics, Sixth edition, Pergaman Press, Oxford, 1980), incorporated herein by reference. Thus, there is a portion of light 26 in which the optic vibrates in the direction of the secondary polarizer 16. The secondary polarizer (analyzer) 16 allows this portion of the light to pass to the photodetector 18. The detected change or amplification in light intensity can be transduced electronically into a perceptible signal.

Figure 2A:
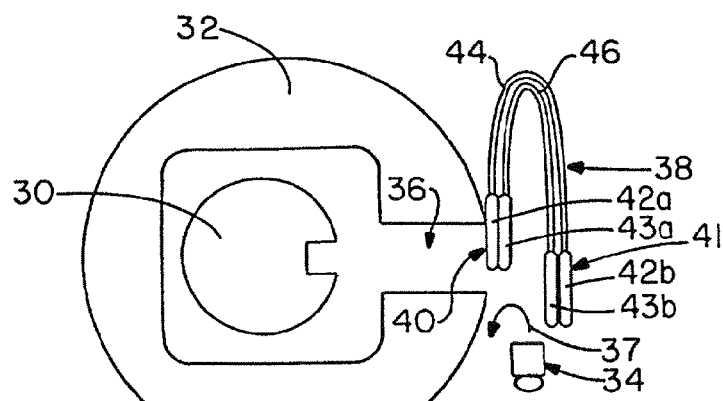
FIG. 2A is a schematic representation of a caged enzyme amplification mechanism in which one or more receptors blocks the channel leading to the enzyme in the absence of a ligand.
Figure 2B:
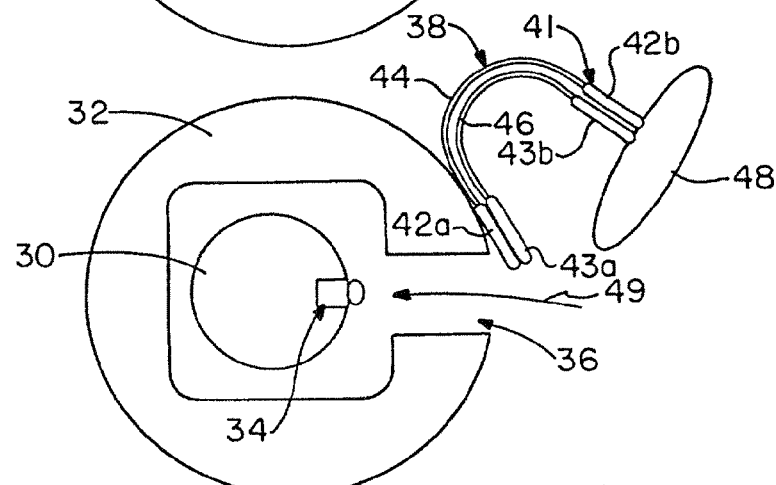
FIG. 2B is schematic representation of a caged enzyme amplification mechanism in which a ligand binds to the receptor causing distortion of the linker region and the unblocking of the channel leading to the enzyme.
Figure 2C:
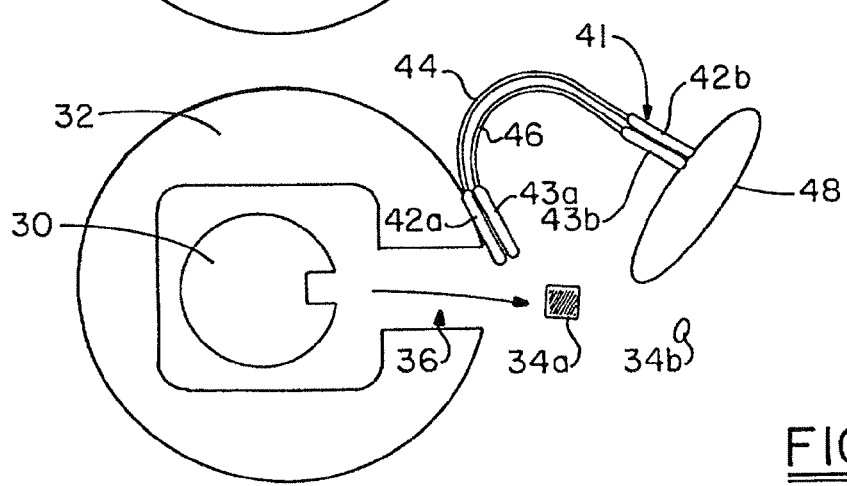
FIG. 2C is a schematic representation of a caged enzyme antibody amplification mechanism in which, once activated by ligand binding to receptor, the channel leading to the enzyme remains open and multiple substrates can interact with the enzyme.

In another embodiment of the present invention, shown schematically in FIGS. 2A-2C, enzyme-substrate interactions are exploited for amplification. With reference to FIG. 2A, an enzyme 30 is entrapped within a cage 32 to prevent premature interaction of enzyme 30 and a substrate 34. Substrate 34 can potentially gain access to enzyme 30 through one or more channels 36 transecting cage 32. Channel 36, however, is blocked as indicated by arrow 37, by one or more receptors having dual binding capacities (diabodies) 38 in the absence of a pathogenic agent.

To produce a diabody, two antibodies are coupled, preferably according to the methods of Holliger et al. (Proc. Natl.

Acad. Sci USA 90:6444, 1993), incorporated herein by reference, to form diabody 38 which has two distinct antigen-binding regions 40 and 41, directed toward channel 36 and a ligand 48, respectively. Ligand-binding region 40 consists of a heavy chain immunoglobulin 42a and a light chain immunoglobulin 43a. Ligand-binding region 41 consists of a heavy chain immunoglobulin 43b and a light chain immunoglobulin 42b. Without intending to be bound by any particular theory, it is believed that the binding of binding region 40 to one or more diabodies 38 to an epitope on cage 32 blocks channel 36 and prevents substrate-enzyme interactions. Thus substrate 34 is not processed under non-stimulated conditions.

With reference to FIG. 2B, when binding region 41 attaches to ligand 48, the linker regions 44 and 46 of diabody 38 are distorted so that channel 36 becomes unblocked and substrate 34 can pass through channel 36, indicted by arrow 49, and interact with enzyme 30. Once activated by ligand 48, channel 36 remains open and multiple substrates 34 can enter and be acted on to produce products 34a and 34b which may be colored products that are chromophoric or flourescent. Either one or both products 34a and 34b are then detected or amplified, and may be transduced into a perceptible signal.

Although one skilled in the art would realize that various globular structures, preferably proteins, could be used as cage 32, alpha-2-macroglobulin is particularly well suited for acting as an enzyme cage because several enzymes, including trypsin and thrombin, will partially degrade alpha-2-macroglobulin, enter the protein, and become entrapped merely by mixing the alpha-2-macroglobulin and enzyme.

Enzyme 30 can be any that can be entrapped in a molecular cage and that produces a detectable change of its substrate. One of ordinary skill in the art would realize that a myriad of enzyme-substrate pairs are detectable and therefore suitable. Thrombin and trypsin, for example, are two preferred enzymes. A preferred substrate has a recognition site and a chromogen such that detectable calorimetric change occurs upon enzyme-substrate binding.

Linker regions 44 and 46 are engineered to allow substrate 34 to enter channel 36 upon binding of ligand 48 to antigen binding region 41. Linker regions 44 and 46 are preferably of moderate length. The skilled artisan would appreciate that if the length of linker regions 44 and 46 are too short or too long, then these regions may not distort adequately to unblock channel 36. The preferred range of linker region length depends primarily on the nature of cage 32 and channel 36.

Linker regions 44 and 46 are also preferably bonded together by ionic, hydrogen, or other bonds. Otherwise, linker regions 44 and 46 would be susceptible to separation and consequently inadequate distortion upon binding of a pathogenic agent.

Figure 3C:
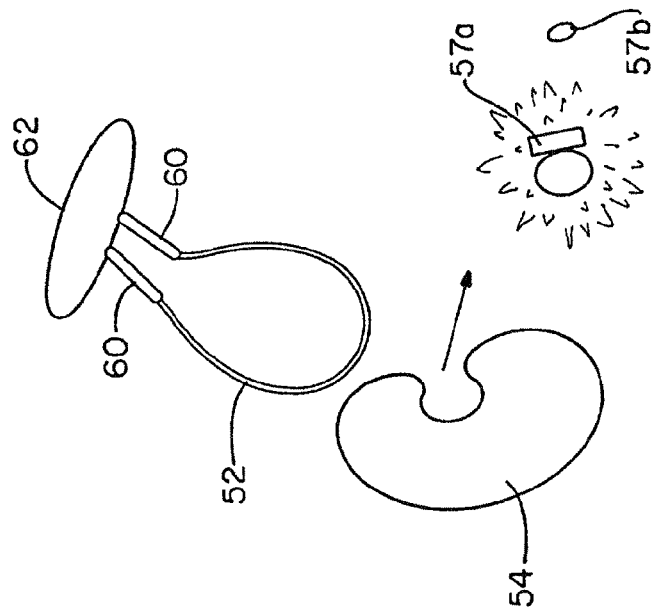
FIG. 3C is a schematic representation of substrate conversion by the enzyme, after picogram levels of ligand bind to the receptor.
Figure 3B:
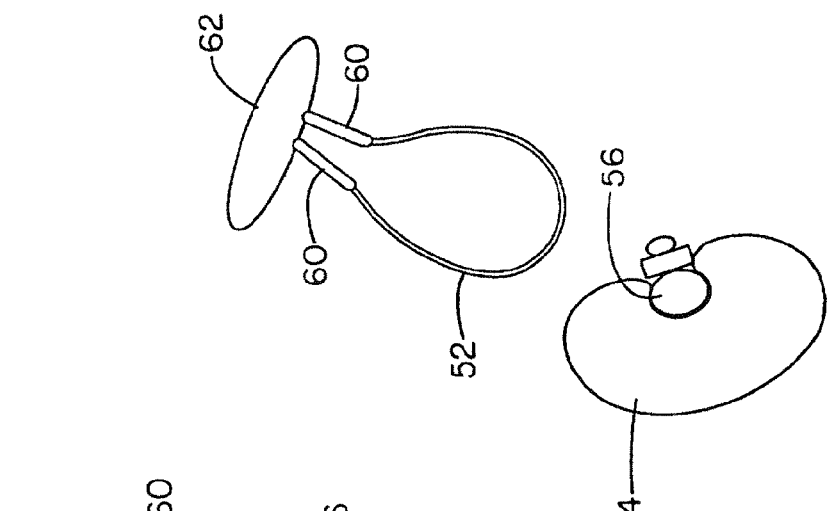
FIG. 3B is a schematic representation of the binding of a ligand to the molecularly-engineered receptor causing dissociation of the receptor from the enzyme, exposing the active site of the enzyme to the substrate.
Figure 3A:
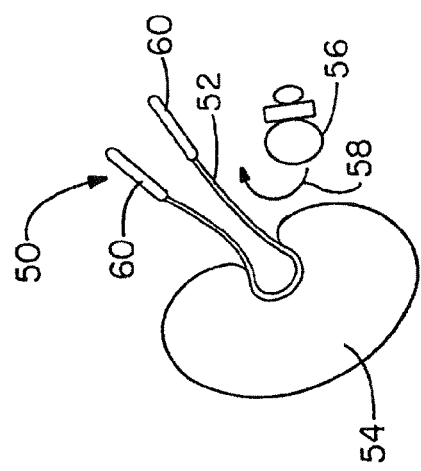
FIG. 3A is a schematic representation of an enzyme inactivated by a molecularly-engineered receptor.

An another embodiment of the present invention, represented schematically in FIGS. 3A-3C, also uses an enzyme-substrate amplification mechanism. As shown in FIG. 3A, a single chain chimeric antibody 50 is engineered such that linker region 52 specifically binds an enzyme 54 to inhibit the binding of a substrate 56 to enzyme 54, as indicated by arrow 58. In this embodiment, linker region 52 has a portion of its polypeptide sequence that is complementary to the active site of enzyme 54. Techniques for the determination of suitable complementary polypeptides are well known.

As shown in FIG. 3B, when a binding region 60 of antibody 50 binds a ligand 62, a conformational change in linker region 52 results in the dissociation of antibody 50 from enzyme 54. Liberated enzyme 54 is now able to act on substrate 56. Each liberated enzyme can react with multiple substrates to provide an amplified signal. By way of example only, a particularly preferred embodiment is depicted in FIG. 3C showing how an enzyme, such as luciferase, can be used to alter its substrate, in this example, the oxidation and dissociation of luciferin. This reaction produces a fluorescent species 57a that is detectable below picogram levels of reaction product, and a non-fluorescent species 57b. Fluorescent species 57a is then detected or amplified and may be transduced into a perceptible signal. Enzyme 54 can be any enzyme that produces a detectable conversion of its substrate.

Experimental

Liquid Crystal Amplification Mechanism

A ligand detection system using a liquid crystal amplification mechanism was developed. A murine antibody to *E. coli* lipopolysaccharide (LPS), a surface antigen found on Gram-negative bacteria, was obtained from a commercial source (Biodesign International, cat. #C61212M, clone #26-5, lot #5D1197) and diluted (1:10) with sterile phosphate-buffered saline (PBS) pH 7.2 to yield a 100 ng/µl sample.

A late log phase culture of *E. Coli* was grown in Brain Heart Infusion (BHI) broth and washed free of growth medium with 0.9% sterile saline. Bacterial numbers (determined by optical density at 600 nm and colony-forming units (CFUs)) were quantitated by extrapolation from growth curve data. Bacteria were then adjusted to $4.6 \times 10^1$ CFU per 5 µl by dilution with sterile saline.

The lyotropic liquid crystalline solution was prepared in a lamellar phase, using hexanol as a co-surfactant to help control the phase state of the mixture. Cetylpiridiniumchloride (CpCl) was combined with hexanol in the proportion hexanol/CpCl=0.651 (w/w). The mixture was then diluted with a saline solution (1% NaCl in water) until 85% of the weight was saline. The resulting liquid crystal was lamellar but close to the micellar phase (Nastishin, Langmuir. Vol. 12, pp. 5011-5015, 1996), incorporated herein by reference. In this phase, the lyotropic liquid crystal is biphilic, and thus is capable of interacting with several different types of receptors.

The tested detection system was created by inserting a receptor (antibody) into the hexanol/CpCl/saline lyotropic liquid crystal. Thus, for each assay, 5 µl of the antibody (500 ng) solution, specifically reactive against *E. coli* (LPS), was added to 5 µl of the lyotropic liquid crystalline solution and mixed. An experimental sample (5 µl) was then added to an aliquot (10 µl) of the liquid crystal-antibody mixture and mixed. The experimental samples were added to the antibody-liquid crystal mixture as follows: Sample A-5 µl of *E. coli* ($4.6 \times 10^1$ CFU), a specific bacteria that the system is designed to detect; Sample B-5 µl of PBS, or Sample C-5 µl ($2 \times 10^6$ CFU) *S aureus*, an irrelevant bacteria that the system should not detect. The samples were centrifuged (3,500×g; 5 sec.) to eliminate bubbles, and 10 µl of the reaction mixture was placed on an ethanol-cleaned microscope slide, covered with an ethanol-cleaned glass cover slip, and the mixture was evaluated for birefringence using polarized light. The experimental conditions and results are summarized in Table 1. Birefringence occurred only when the antibody was bound to its specific antigen, with visually discernable changes in birefringence detected for bacteria concentrations as low as 46-460 CFU per 5 µl.

TABLE 1

| Sample | Antibody (LPS) | E. coli | S. aureus | PBS | Liquid Crystal | Birefringence |
|---|---|---|---|---|---|---|
| A | 500 ng | $4.6 \times 10^1$ | — | — | 5 μl | YES |
| B | 500 ng | — | — | 5 μl | 5 μl | NO |
| C | 500 ng | — | $2 \times 10^6$ | — | 5 μl | NO |

Figure 4A:
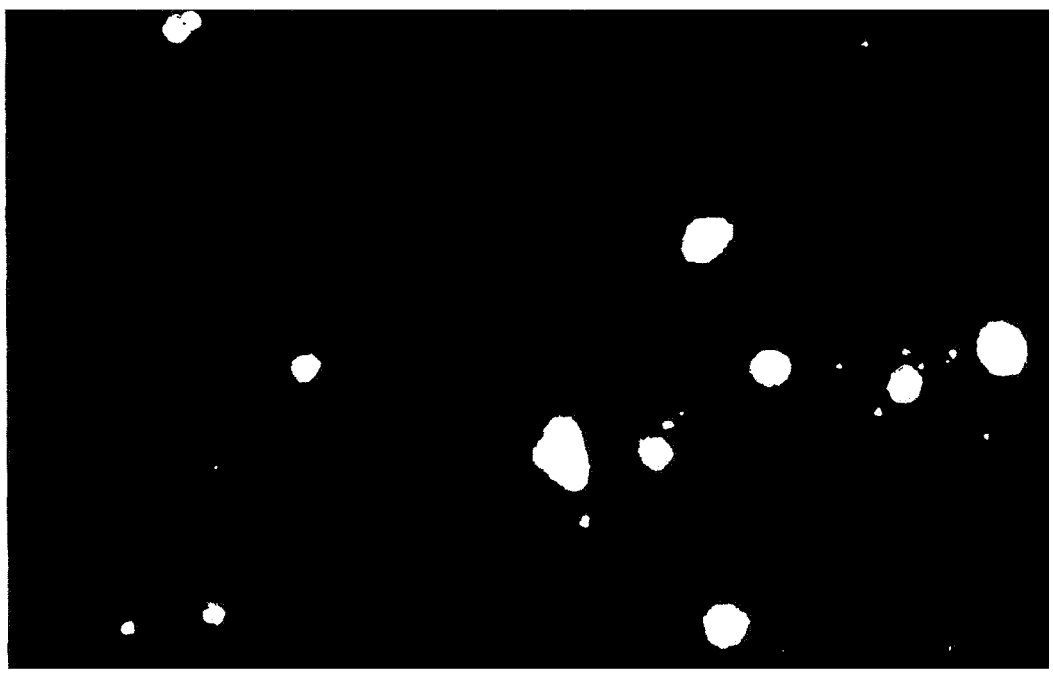
FIG. 4A is a photograph showing the birefringence of polarized light through a liquid crystal-receptor array in response to binding of a specific ligand to the receptor.
Figure 4B:
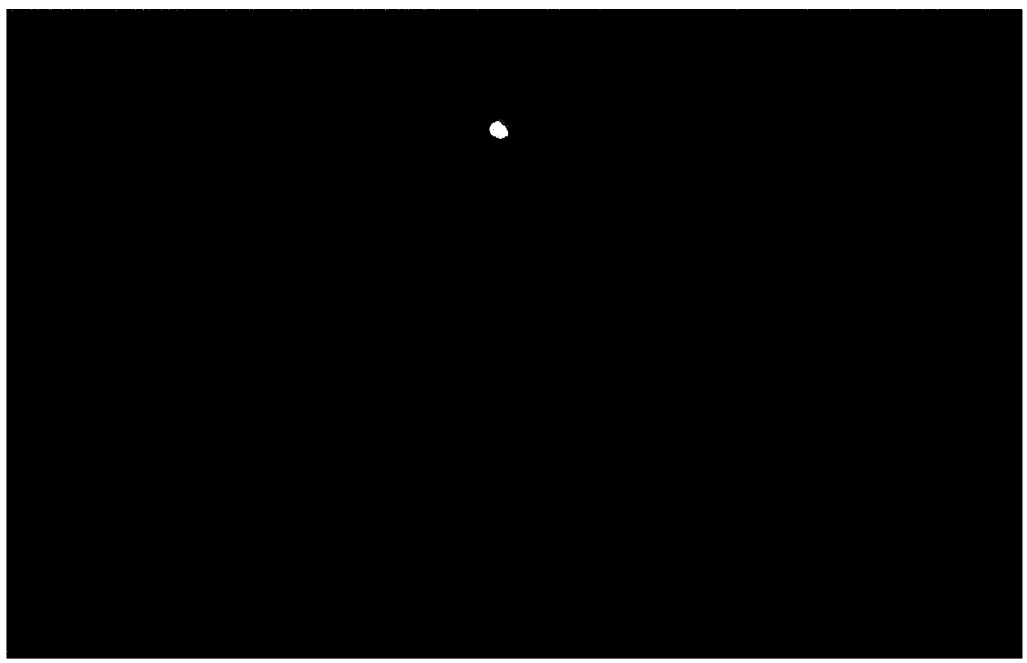
FIG. 4B is a photograph showing the absence of birefringence of polarized light through a liquid crystal-receptor array in a reaction mixture containing liquid crystal, receptor and PBS.
Figure 4C:
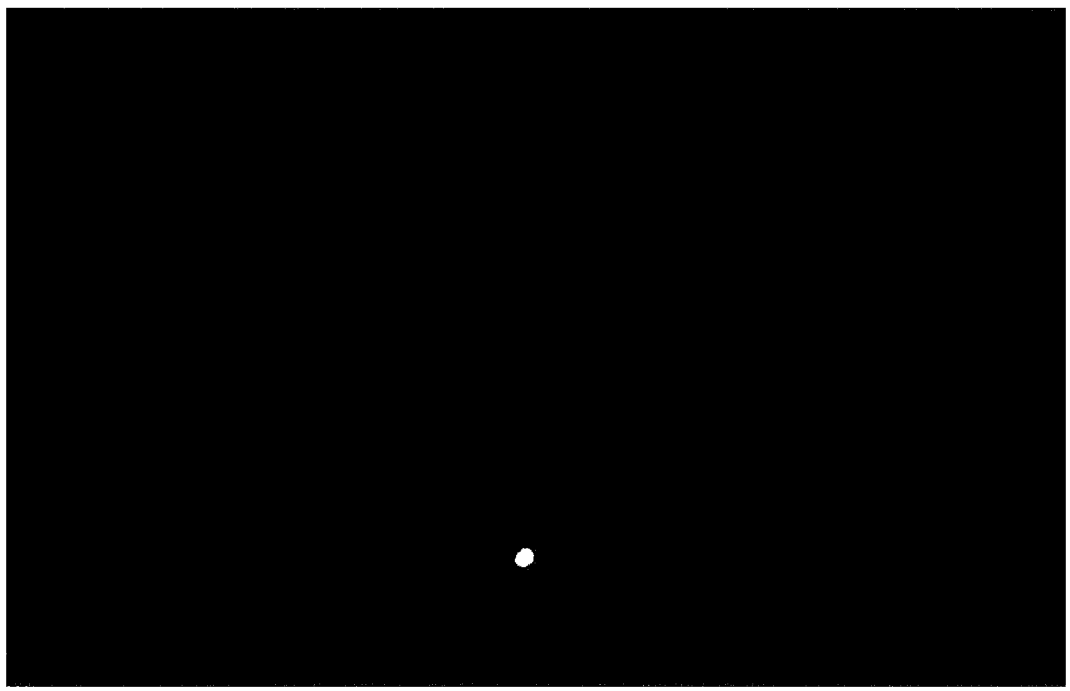
FIG. 4C is a photograph showing the absence of birefringence of polarized light through a liquid crystal-receptor array in a reaction mixture containing liquid crystal, receptor and an irrelevant ligand.

In other experiments, LPS antibody, E. Coli (2.7×10$^7$ CFU) and liquid crystalline material were reacted in a manner similar to the previous experiment, and representative photomicrographs (10× magnification; FIGS. 4A, 4B and 4C) were evaluated with a Bio-Quant Image Analysis System. The image analysis was performed to quantatively compare propagating light transmission when E. coli, PBS or S. aureus was evaluated by the receptor-ligand binding system. The photographic images were digitized and integrated optical density (IOD) automatically calculated according to the following formula:

$$IOD = \frac{(\Sigma - \log_{10})(\text{foreground})}{(\text{background})}$$

Figure 5:
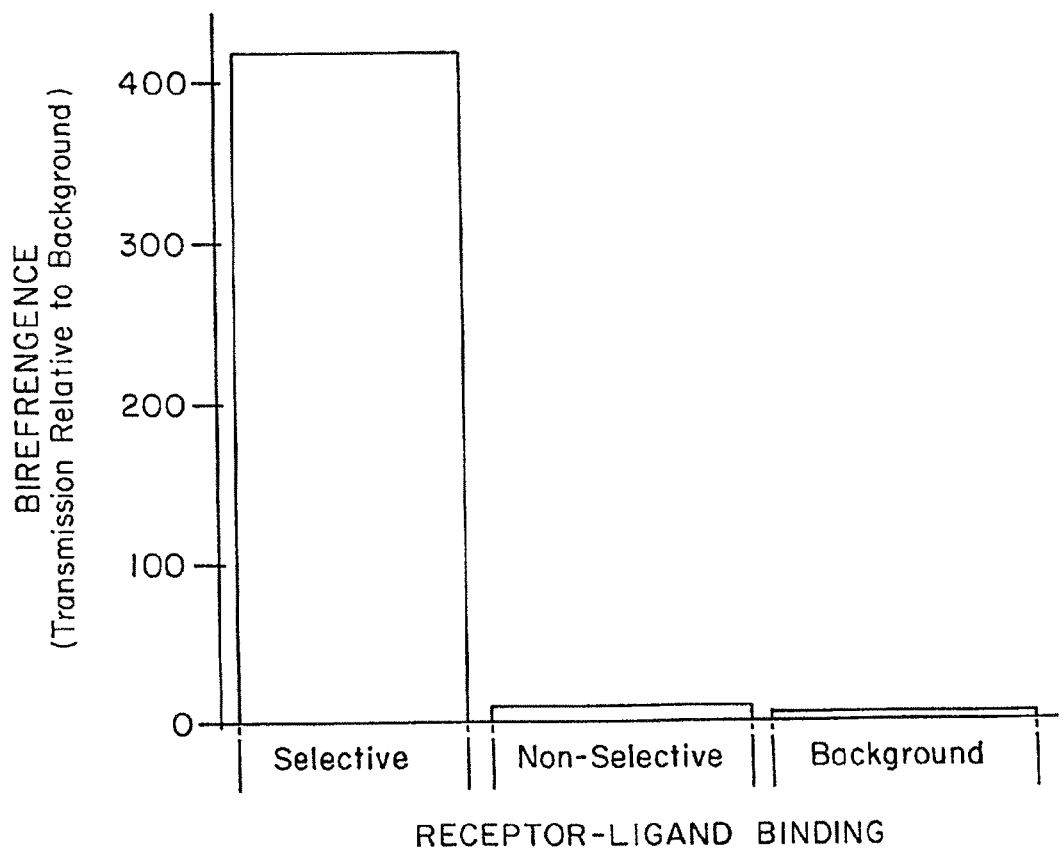
FIG. 5 is a graph showing the quantative analysis of the birefringence of polarized light through an liquid crystal-receptor array of the ligand detection system for selective receptor-ligand binding, as compared to non-selective receptor-ligand binding and background receptor-ligand binding.

The resulting data, presented in FIG. 5, show that a profound increase in transmission of propagating light occurs when liquid crystals amplify the binding of antibody to E. coli (LPS).

Caged Enzyme Amplification Mechanism

Figure 6A:
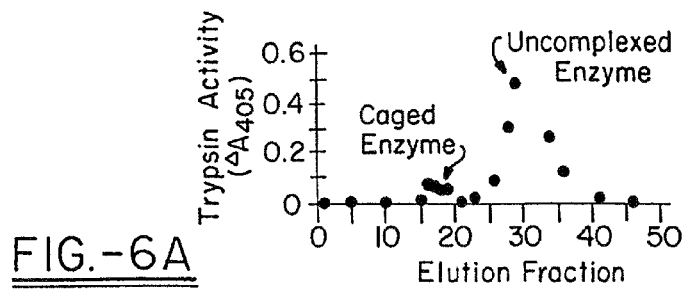
FIG. 6A is a graph showing enzymatic activity of elution fractions containing an alpha-2-macroglobulin-trypsin complex.
Figure 6B:
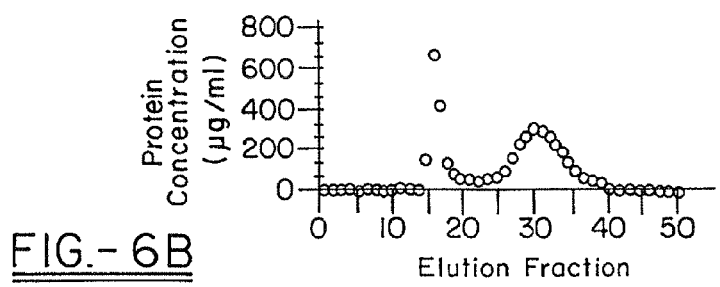
FIG. 6B is a graph showing the protein concentration (ug/ml) of elution fractions containing an alpha-2-macroglobulin-trypsin complex.

The sensitivity of an alpha-2-macroglobulin amplification mechanism was demonstrated. Standard 2 mg/100 μl solution of human alpha-2-macroglobulin ($\alpha_2$ M, Calbiochem Co., product number 441251), trypsin (Sigma Chemical Co., T-8003) and thrombin (Sigma Chemical Co., T-4648) were made by dissolving the protease or antiprotease in 0.1 M HEPES buffer (pH 7.6). Equal volumes (100 μl) of $\alpha_2$M and one of the enzymes were mixed, permitted to interact for ten minutes at room temperature and then cooled to 4° C. The 200 μl sample was added to a gel filtration column (1 cm×24 cm; 18.8 ml bed volume; 0.44 ml/min flow rate; located in a 4° C. cold room) packed with Sephadex G-100 to separate the caged enzyme from uncomplexed enzymes. Column eluent was collected in 1.0 ml fractions. Changes in light absorbance at 280 nm was measured to determine the protein concentration in each fraction and enzymatic activity was determined to identify those fractions containing the caged enzymes. The results of those measurements, shown in FIGS. 6A and 6B, demonstrate that fractions 15-17 contained relatively pure samples of caged enzyme. Those fractions were used for the subsequent evaluations.

Figure 6C:
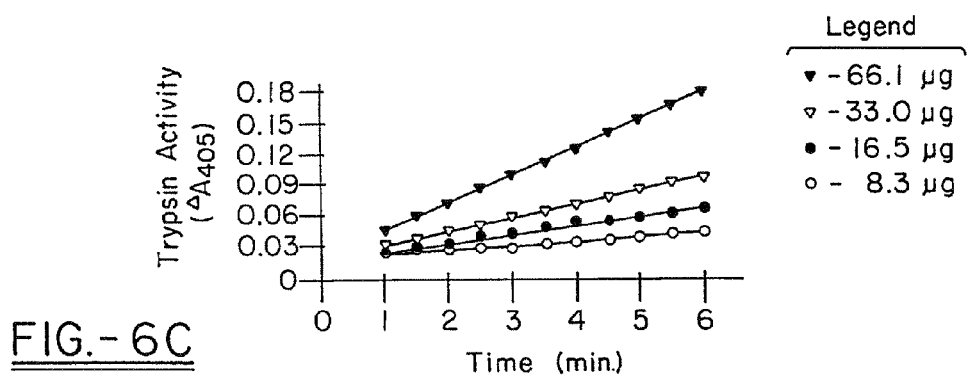
FIG. 6C is a graph showing the effect of the concentration of caged trypsin on detectable enzymatic activity over time (min.).
Figure 6D:
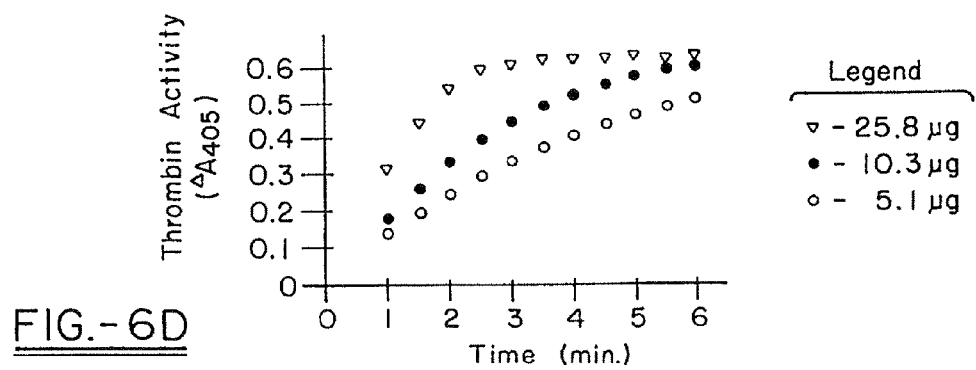
FIG. 6D is a graph showing the effect of the concentration of caged thrombin on detectable enzymatic activity over time (min.).
Figure 6E:
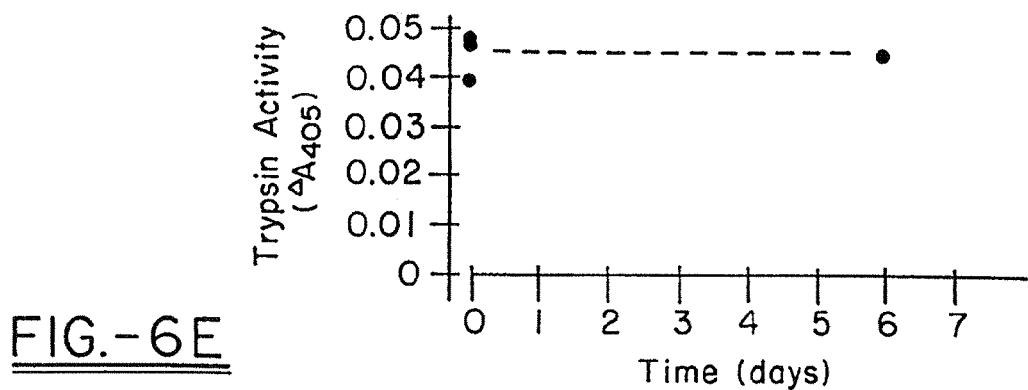
FIG. 6E is a graph showing the stability of caged trypsin over time (days).

Small synthetic substrates, N-benzoyl-L-arg-p-nitroanalide and N-p-tosyl-gly-pro-arg-p-nitroanalide, were used to define the enzymatic activities of caged trypsin (FIG. 6C) and caged thrombin (FIG. 6D), respectively. While both systems exhibited dose-response characteristics, the caged thrombin exhibited greater sensitivity. The enzymatic activity did not degrade with time. The enzymatic activity of the caged trypsin was unchanged following six days of storage at 4° C. (FIG. 6E). Similarly, caged thrombin activity was also stable when measured 24 hours following preparation.

Luciferase Amplification Mechanism

Figure 7A:
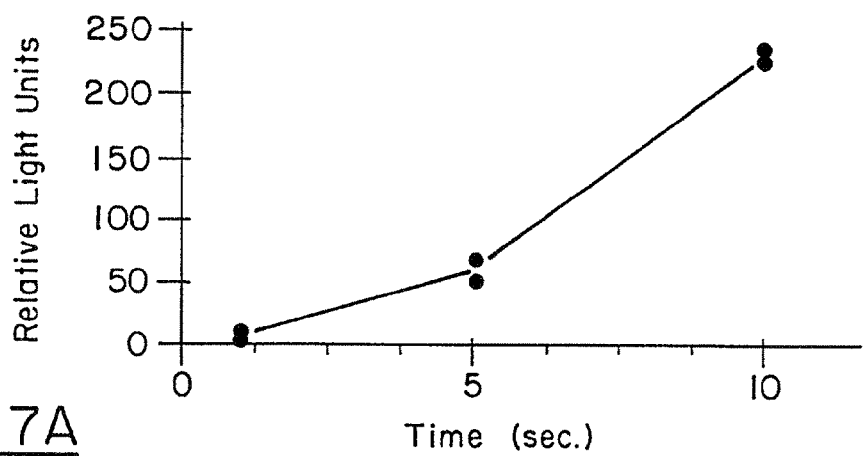
FIG. 7A is a graph showing luciferase activity (Relative Light Units) over time (sec.).
Figure 7B:
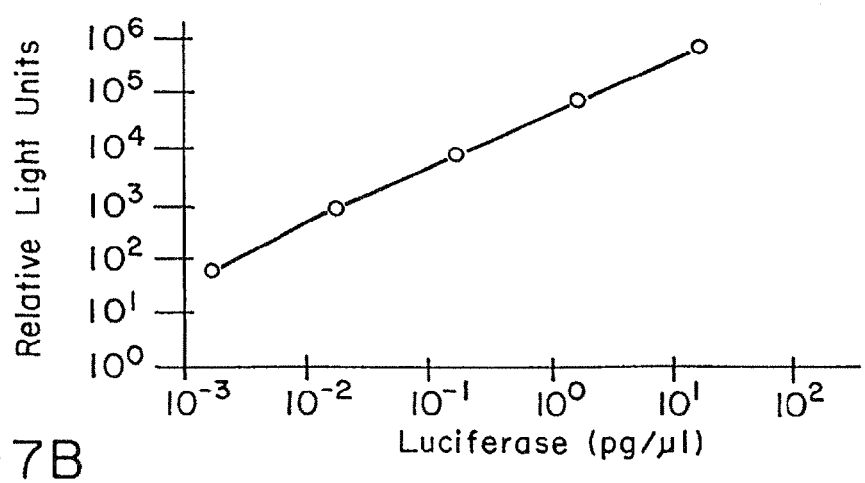
FIG. 7B is a graph showing luciferase activity (Relative Light Units) as a function of luciferase concentration (pg/ul).

The exceptional sensitivity of a luciferase-based amplification mechanism was demonstrated using a Berthold Lumat Luminometer. Varying amounts of luciferase (4 mg/ml of 0.15% NaCl, 10 mM HEPES, 1 mM EDTA, 2 mM MgCl$_2$, 2 mM dithiothreitol; Sigma Chemical Co.) were added to the luminometer reaction chamber. The enzymatic reaction was initiated by rapid injection of 0.5 mM luciferin (Promega, E1483), 0.5 mM adenosine triphosphate (Sigma Chemical Co., A-7699), 5 mM MgSO$_4$, 1.0 mM dithiothreitol (Sigma Chemical Co.) in 50 mM HEPES buffer (pH 7.8) into the reaction chamber. FIG. 7B shows that detectable luciferase activity can be measured with an enzyme concentration of only 0.0017 pg/μl, and linear increases in activity are observed with progressive elevations in enzyme concentration.

It is to be understood that any variations evident fall within the scope of the claimed invention, and thus the selection of specific antibodies, caged enzymes, receptor-inactivated enzymes or liquid crystals can be determined without departing form the spirit of the invention herein disclosed and described. It should also be understood that the present invention, while particularly suited for pathogen detection, is intended to include the detection of any ligand. Moreover, the scope of the invention shall include all modifications and variations that may fall within the scope of the attached claims.

What is claimed is:

1. A device for the detection of ligands comprising:
   an amplification mechanism comprising an enzyme entrapped within a biological cage having at least one channel located therein, wherein the biological cage is alpha-2-macroglobulin;
   at least one receptor bound to said biological cage, said receptor capable of binding to a ligand to form a receptor-ligand complex, wherein the at least one receptor is attached to the biological cage such that the at least one receptor blocks the channel prior to formation of the receptor-ligand complex;
   wherein an amplified signal is produced from said enzyme interacting with a plurality of substrate molecules upon receptor-ligand complex formation.

2. The device of claim 1, wherein the receptor is an antibody.

3. The device of claim 2, wherein the antibody is selected from the group consisting of monoclonal, polyclonal, and molecularly engineered antibodies.

4. The device of claim 1, wherein the receptor is a diabody having a ligand binding region and a cage binding region connected by a linker region.

5. The device of claim 1, wherein formation of the receptor-ligand complex unblocks the channel permitting the substrate molecules to pass through the channel.

6. The device of claim 1, wherein the receptor is a diabody and wherein the ligand is a pathogenic agent.

7. The device of claim 1, wherein the enzyme is selected from the group consisting of thrombin and trypsin and luciferase.

8. The device of claim 7, wherein the enzyme is trypsin.

9. The device of claim 1, wherein the enzyme is thrombin.

10. The device of claim 1, wherein receptor binds to a specific ligand.

* * * * *